(12) United States Patent
Ziegler et al.

(10) Patent No.: US 7,066,007 B2
(45) Date of Patent: Jun. 27, 2006

(54) SYSTEMS AND METHODS FOR PREDICTING THE BENDING STIFFNESS OF WOOD PRODUCTS

(75) Inventors: Gerald A. Ziegler, Orting, WA (US); Michael J. Yancey, Puyallup, WA (US)

(73) Assignee: eyerhaeuser Company, Federal Way, WA (US)

( * ) Notice: Subject to any disclaimer, the term of this patent is extended or adjusted under 35 U.S.C. 154(b) by 118 days.

(21) Appl. No.: 10/688,350

(22) Filed: Oct. 17, 2003

(65) Prior Publication Data

US 2005/0086023 A1    Apr. 21, 2005

(51) Int. Cl.
G01N 3/30       (2006.01)
G01N 33/46      (2006.01)

(52) U.S. Cl. .......................... 73/12.12; 73/597; 73/602

(58) Field of Classification Search ............... 73/12.12, 73/12.09, 579–583, 597–600, 601–602, 574, 73/622, 862.59, 801; 378/54, 86–87, 89–90
See application file for complete search history.

(56) References Cited

U.S. PATENT DOCUMENTS

| | | | | |
|---|---|---|---|---|
| 4,879,752 A | * | 11/1989 | Aune et al. | 382/141 |
| 4,941,357 A | * | 7/1990 | Schajer | 73/600 |
| 5,023,805 A | * | 6/1991 | Aune et al. | 702/38 |
| 5,024,091 A | * | 6/1991 | Pellerin et al. | 73/597 |
| 5,394,342 A | * | 2/1995 | Poon | 702/137 |
| 5,564,573 A | * | 10/1996 | Palm et al. | 209/518 |
| 6,151,379 A | * | 11/2000 | Kullenberg et al. | 378/54 |
| 6,347,542 B1 | * | 2/2002 | Larsson et al. | 73/12.12 |

FOREIGN PATENT DOCUMENTS

| | | |
|---|---|---|
| CA | 2235093 A1 * | 10/1999 |
| DE | 4435975 A1 * | 4/1995 |
| WO | WO 200109603 A1 * | 2/2001 |
| WO | WO 200177669 A1 * | 10/2001 |
| WO | WO 2002060662 A2 * | 8/2005 |

* cited by examiner

Primary Examiner—Hezron Williams
Assistant Examiner—Rose M. Miller
(74) Attorney, Agent, or Firm—Christensen O'Connor Johnson Kindness

(57) ABSTRACT

Generally described, a bending stiffness predicting system 20 includes a density measurement sub-system 24 and a sound wave velocity measurement sub-system 28. From the measurements of both density and speed of sound through the wood product received from the sub-systems 24 and 28, respectively, the bending stiffness (Y) may be predicted by calculating the bending stiffness (Y) according to the bending stiffness (MOE) equation: $Y = k\rho V^2/g$; wherein k is the calibration constant, $\rho$ is the density or specific gravity of the member, V is the velocity of a sound through the member and g is the acceleration due to gravity. The calculation of wood product bending stiffness may be carried out manually, or may be calculated using a calculating sub-system 32 from the two measured values, density and velocity, according to Equation 1 above.

20 Claims, 5 Drawing Sheets

DIRECTION OF WAVE MOTION

SYSTEMS AND METHODS FOR PREDICTING THE BENDING STIFFNESS OF WOOD PRODUCTS

FIELD OF THE INVENTION

The present invention relates to non-destructive systems, and particularly, to systems that non-destructively determine the bending stiffness of objects, such as wood products.

BACKGROUND OF THE INVENTION

Efficient utilization of lumber production requires that the material be graded according to its intended use. In this way, an effective and economic match can be made between the lumber needs of end-users and the lumber supplier of the product. Many factors control the suitability of lumber for any particular purpose. They include the degree of straightness, the amount of any wane, and the presence and size of knots, splits, shakes, etc. These and other factors are currently assessed by trained personnel using established visual grade rules.

Several engineering properties, including tensile strength, bending strength, and bending stiffness are of great importance when designing wood structures and factor greatly in the suitability of a particular piece of processed lumber for a specific application. For example, lumber having a high bending stiffness or Modulus of Elasticity (MOE) is worth more than lumber with low MOE, since lumber with a higher MOE can be used in such applications as floor joists or roof trusses, which span over a longer distance, or provide a "stiffer" floor or roof over the same span is needed or required.

In the visual system of grading, these aforementioned properties have been established from destructive tests on extensive samples of each visual grade, species, and size of lumber. Mechanical grading on the other hand, indirectly measures these properties on each piece, and is independent of species and size of the material. The process of visual grading includes a wide range of wood strength and bending stiffness. Thus, a sample of material of a given visual grade contains pieces whose strengths and bending stiffness vary over very wide ranges. For example, the strength of the strongest piece in a batch of a given visual grade is typically 5–10 times that of the weakest piece. Thus, for safe design, a near minimum strength of the population has to be assumed. This is clearly very wasteful of the majority of superior pieces which are being used at well below their actual capacities. In addition, these properties vary according to the species and size of the material.

Such waste can be reduced by developing and using techniques which better identify the superior pieces and reliably distinguish them from the inferior pieces. One such non-destructive technique has been developed to overcome the deficiencies of visual inspection, yet still provide a determination of mechanical properties in the wood product. This technique employs X-ray imaging to measure the density of the wood product, and to image defects such as knots. From the measurement of density, the bending stiffness of the wood produce can be inferred. In addition, by taking into consideration the size and location of the defects, the strength of the wood product can be estimated.

The X-ray imaging technique, however, has the drawback that density determined by X-rays is not completely indicative of strength, nor can bending stiffness be reasonably inferred from only the density. In particular, there are growing conditions in which the density of the wood is "normal", and yet the boards have low bending stiffness. Biological deterioration can degrade the mechanical properties of wood, yet does not change the density of wood. One such condition is "compression wood", which is caused by trees growing on steep hills, or in regions of constant prevailing winds in a specific direction. In these cases, the wood has different structural properties on the uphill (upwind) side and the downhill (downwind) side of the tree. Another condition is when wood products are manufactured from young plantations. This material produces another condition in which the density within the tree may appear "normal", yet the bending stiffness of the wood product varies tremendously. Such plantation wood typically has similar densities as old growth trees of the same dimensions, but typically includes a higher percentage of wood that exhibits juvenile characteristics, which includes a greater microfibril angle and varying quantities of chemicals. Wood products having higher concentrations of juvenile characteristics are prone to having extreme variations in bending stiffness.

Therefore, there is a need in the wood products industry for improved systems and methods that can predict the bending stiffness of wood products.

SUMMARY OF THE INVENTION

Embodiments of the present invention are improved methods and systems for predicting bending stiffness of wood products in most stages of breakdown from log form to finished dimension lumber. The systems and methods involve a two-stage process of measuring of the density of the wood along its length, and measuring the velocity of an induced sound wave as it travels through the wood along its length. From these measurements, the bending stiffness of the wood product is calculated.

In accordance with aspects of the present invention, a method for nondestructively testing an object is provided. The method includes measuring the density of an object by detecting radiation absorption in the object, and measuring the velocity of a sound wave propagating through the object. From the density and sound wave velocity measurements, a value of the object mechanical property is calculated. The calculated value is indicative of the bending stiffness of the object.

In accordance with another aspect of the present invention, a method for calculating the bending stiffness in a wood product is provided. The method includes emitting radiation in the direction of the wood product transverse to the longitudinal axis thereof, and detecting radiation that passes through the wood product. The density of the wood product is determined based on the detected radiation. A sound wave is induced into the wood product, the induced sound wave is sensed, and the velocity of the induced sound wave based on the sensed induced sound wave is determined. The bending stiffness of the wood product is then calculated based on the determined density and determined velocity.

In accordance with still another aspect of the present invention, a system for non-destructively calculating the bending stiffness in a wood product is provided. The system includes a density measurement sub-system composed of a radiation source positioned transverse to the longitudinal axis of the wood product and a radiation detector positioned on the side of the wood product opposite the radiation source. The radiation detector generates signals indicative of detected radiation, wherein the generated signals are pro cessed to calculate the density of the wood product. The system also includes a velocity measurement sub-system composed of a sound wave device that induces a sound wave in the wood product and a receiving sensor that measures the arrival of the induced sound wave in the wood product and generates signals indicative thereof. The receiving sensor generated signals are processed to calculate the velocity of the induced sound wave. The stiffness in the wood product is calculated based on the calculated sound wave velocity from the velocity measurement sub-system and the density measurement from the density measurement sub-system.

BRIEF DESCRIPTION OF THE DRAWINGS

The foregoing aspects and many of the attendant advantages of this invention will become more readily appreciated by reference to the following detailed description, when taken in conjunction with the accompanying drawings, wherein.

DETAILED DESCRIPTION OF THE PREFERRED EMBODIMENTS

Embodiments of the present invention will now be described with reference to the accompanying drawings where like numerals correspond to like elements. The present invention is directed to systems and methods for predicting the Modulus of Elasticity (MOE), otherwise known as bending stiffness, of wood products using non-destructive evaluation techniques. Specifically, the present invention is directed to wood product testing systems and methods that measures density and the velocity of sound waves in a wood product. Such systems and methods may be suitable for incorporation into timber grading machines located in timber mills. By determining the bending stiffness in wood products in this manner, more accurate results may be achieved than current systems, resulting in better utilization of the wood products, and higher profitability to wood processors. The terms "wood products" or "wood containing products" are used herein to refer to trees, logs, lumber, boards and wood composites or engineered wood in various stages of processing. However, it will be appreciated that the systems and methods of the present invention may be utilized for determining the bending stiffness of other rigid materials, such as concrete products, steel, plastics, gypsum, to name a few. Accordingly, the embodiments of the present invention that are described herein are illustrative in nature, and should not limit the scope of the present invention, as claimed.

Figure 1:
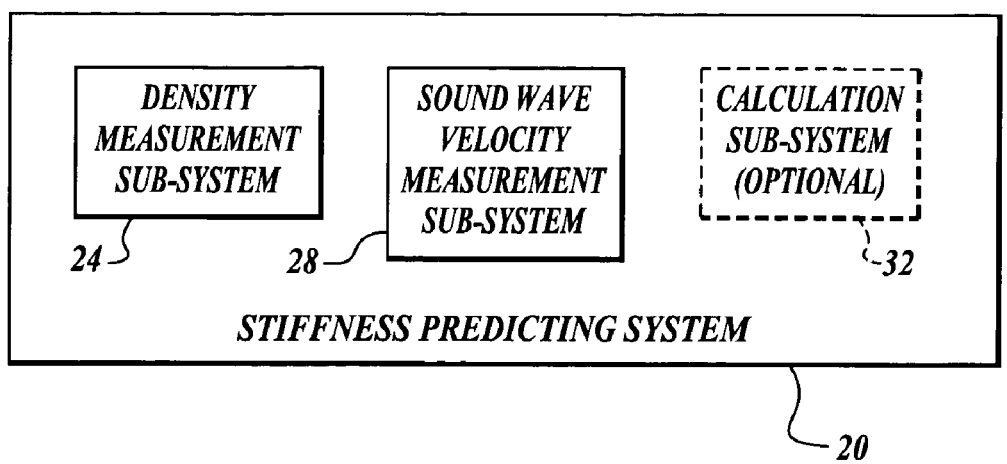
FIG. 1 is a block diagram of a bending stiffness prediction system constructed in accordance with the present invention.

FIG. 1 is a block diagram of one bending stiffness predicting system, generally designated 20, constructed in accordance with principles of the present invention. Generally described, the system 20 includes a density measurement sub-system 24 and a sound wave velocity measurement sub-system 28. From the measurements of both density and speed of sound through the wood product received from the sub-systems 24 and 28, respectively, the bending stiffness (Y) may be predicted by calculating the bending stiffness (Y) according to the following known equation (1) for bending stiffness (MOE).

$$Y = k\rho V^2/g; \qquad (1)$$

wherein k is a calibration constant, ρ is the density of the member, V is the velocity of a sound through the member, and g is the acceleration due to gravity.

The calculation of wood product bending stiffness may be carried out manually, or may be calculated using a calculating sub-system 32 that includes known processing circuitry that is capable of calculating bending stiffness from the two measured values according to Equation 1 above.

Figure 2:
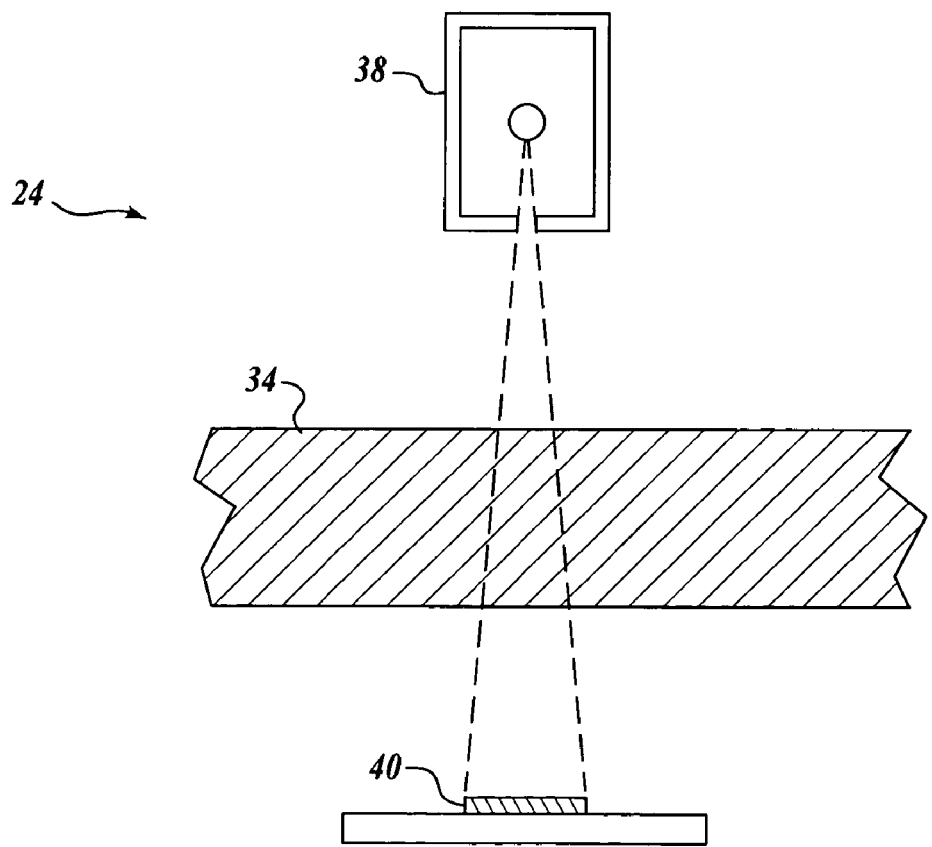
FIG. 2 is a schematic view of a wood product placed in-between a radiation source and a radiation detector.

FIG. 2 shows one embodiment of the density measurement sub-system 24 in which a cross-section of a wood product 34 is situated between a radiation source 38 and a radiation detector 40. The radiation source can be of any suitable type that emits either x-rays or gamma rays. Likewise, the detector 40 may be of any suitable type, for example, an ionization chamber with a scintillation counter, or a diode array. As is known in the art, radiation from the source penetrates the wood product 34, some being absorbed in the wood product 34, and some passing through. The amount of the radiation which emits from the radiation source 40 and passes through the wood product 34 is measured by the detector 38.

Figure 3:
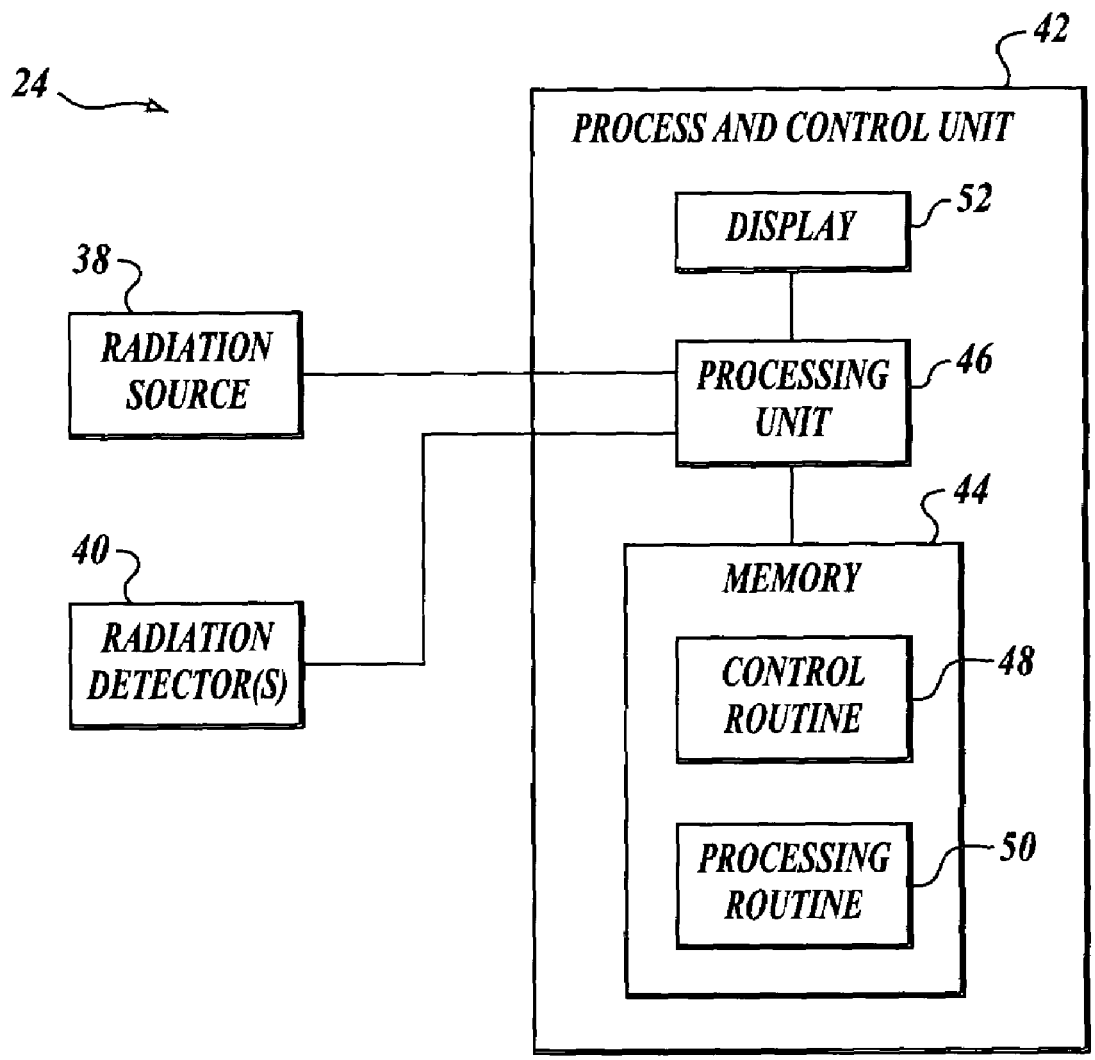
FIG. 3 is a block diagram illustrating the density measurement sub-system.

The measurements from the detector 40 are sent to a process and control unit 42, shown in FIG. 3, which includes a memory 44 and a processing unit 46. The processing unit 46 executes conventional control and processing routines 48 and 50, respectively, which are stored in memory 44. The control routine 48, when executed by the processing unit 46, transmits a control signal to the radiation source 38 to emit the radiation that is subsequently absorbed by the detector 40. The absorption measurements are then processed by the processing routine 50 for determining the density profile of the wood product 34. It will be appreciated that absorption measurements may be repeated in increments along the wood product length to establish transverse local density profiles, and/or a mean density may be determined from the incremental density measurements.

The processing routine 50 determines the density of each tested area of the wood product 34 by a known equation that will now be explained. For nuclear radiation, the radiation intensity which is measured by the detector depends on the source strength, the local density of the wood material through which the radiation passes, the length of the radiation path within the wood, and a material-dependent constant. Mathematically, this dependence can be expressed by Equation (2) below:

$$I/I_o = e^{-\rho\mu h}; \text{ where} \qquad (2)$$

ρ=local wood density (g/cm³);
μ=attenuation coefficient,
e=base of natural logarithms h=wood thickness, cm I=radiation intensity passing through the wood, counts/cm$^2$/s $I_o$=radiation intensity with no wood present, counts/cm$^2$/s Solving for density, the Equation (2) becomes Equation (3):

$$\rho = -ln(I/I_o)/\mu. \qquad (3)$$

Accordingly, the processing unit 46 executes the processing routine 50, which determines the density of the wood product according to Equation (3). Once the processing unit 46 has processed the detector signals and calculated a density value, the density value may be displayed on the display 52, and/or may be saved in memory 44 for later recall or processing.

For a more detailed description of a system that determines the density of wood products using radiation techniques, please see U.S. Pat. No. 4,941,357, which is hereby incorporated by reference. One commercially available machine that may be utilized by the sub-system 24 is the X-ray Lumber Gauge (XLG), available from COE/Newnes McGehee, Salmon Arm, British Columbia. It should be clear that many different geometrical configurations of single or multiple radiation sources and detectors could be chosen that could achieve density profile measurement objectives functionally equivalent to those described above.

Figure 4:
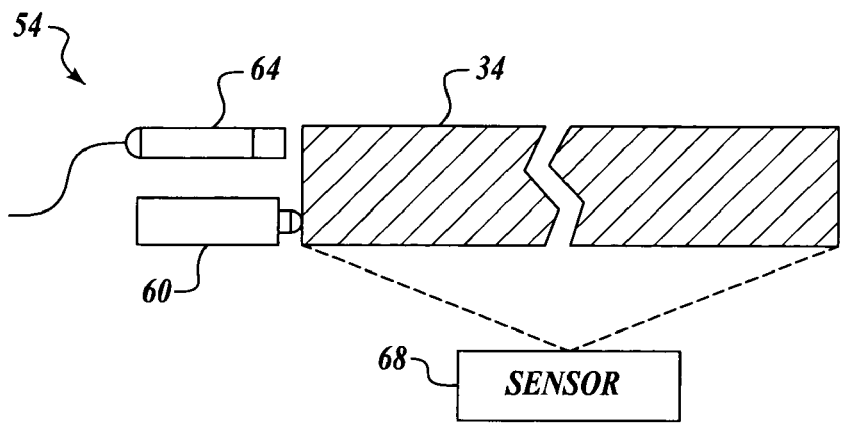
FIG. 4 is a schematic view of one embodiment of the stress wave acquisition unit.
Figure 5:
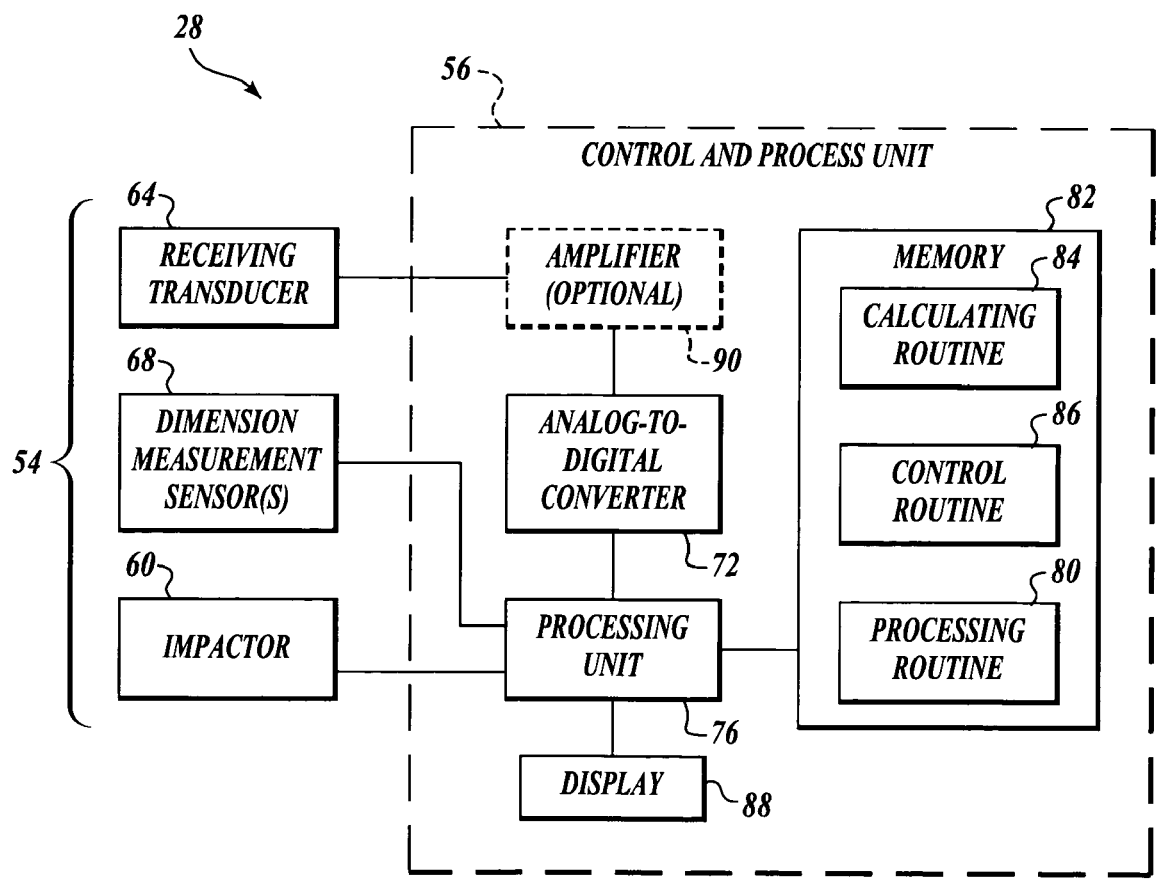
FIG. 5 is a block diagram that illustrates one embodiment of the velocity measurement sub-system.

Turning now to FIG. 5, the bending stiffness predicting system includes a velocity measurement sub-system 28 that measures the velocity of traveling sound waves through the wood product 34 (see FIG. 4). In one embodiment of the present invention, the velocity measurement sub-system 28 includes a stress wave acquisition unit 54 that induces a stress wave into the wood product 34 and produces signals associated with the induced stress wave in the wood product. The sub-system 28 additionally includes a control and process unit 56 that receives the electronic signals produced by the stress wave signal acquisition unit 54. As best shown in FIG. 4, the stress wave acquisition unit 54 includes an impactor 60 that strikes the end of the wood product 34 to induce a stress wave along the length dimension of the wood product 34. The impactor 60 may be any suitable hydraulic or pneumatic hammer, or any other conventional or future developed device that is capable of manual or computer controlled actuation to induce a stress wave into the wood product 34. The stress wave acquisition unit 54 further includes a receiving transducer 64 that picks up the vibrational signals from the stress wave induced into the wood product 34.

The transducer 64 may be a contactless microphone suitably arranged for recording the frequency spectrum of the stress waves in the wood product 34. Specifically, the microphone may be placed so that it, at the impact moment, can collect the radiated acoustic pressure from the end of the wood product 34, originating from the resonance vibrations generated by the impact of the impactor 60. Alternatively, the transducer 64 may be any suitably known accelerometer, for example, an accelerometer of the piezo-electric type, or a laser-based sensor known in the art that can measure the longitudinal vibrations of the wood product 34. A length measurement sensor 68 that utilizes known laser optical scanning techniques to measure the length of the tested wood product 34 may also be included in the stress wave acquisition unit 54 if the wood product length is not already pre-selected or determined by sensing or scanning devices located upstream or downstream in the wood product processing line. The sensor 68 transmits the measurement signal to the control and process unit 56.

The stress wave control and process unit 56 controls the actuation of the impactor 60 and processes the signals received from the transducer 64. FIG. 5 is a block diagram that illustrates the control and process unit 56. The control and process unit 56 includes an analog-to-digital converter 72 and a processing unit 76 that executes a processing routine 80 stored in memory 82. The analog-to digital converter 72 receives analog signals associated with the induced stress wave, and converts the analog signals into digital signals that may be processed by the processing unit 76. It will be appreciated that the sampling rate of the analog-to-digital converter is sufficient to accurately retain the frequency and amplitude content of the analog signals. The processing unit 76 receives the digitized signals from the analog-to-digital converter 72, performs a Fourier transform on the digitized signals, and creates an acoustic pressure spectrum by executing the processing routine 80. The processing routine 80 implements known algorithms that scan the spectrum for the resonance frequency of the induced stress wave.

In some applications of the sub-systems, the unit 56 may include an amplifier 90 for amplifying the analog signal received by the transducer before transmitting the signal to the analog-to digital-converter 72. It will be appreciated that other electrical circuitry may also be employed, such as filters. The memory 82 may also store a calculating routine 84 and a control routine 86, which are executed by the processing unit 76.

To determine the velocity of a stress wave in the wood product 34, the control and process unit 56 causes the impactor 60 to induce a self-propagating stress wave into the wood product 34 by execution of the control routine 86. The vibrations caused by the stress wave are detected by the receiving transducer 64 and transmitted to the processing unit 76 via the analog-to-digital converter 72. Once the signals are received by the processing unit 76, the processing unit 76 processes the signals according to the processing routine 80, which scans for the resonant frequency of the induced stress wave. Once the resonant frequency (f) is located, the stress wave velocity is calculated by the calculating routine 84.

The calculating routine 84 determines the velocity of the stress wave induced into the wood product 34 by a known equation that will now be explained. The velocity of the stress wave induced by the impactor 60 is first measured by determining the time it takes the stress wave to travel to the end of the wood product 34 and back according to equation (4):

$$V = 2L/\tau, \qquad (4)$$

where V is the velocity or speed of the stress wave, L is the length of the wood product and $\tau$ is the round trip time.

In the frequency domain, the time for the stress wave to travel to the end of the wood product and back is related to the resonance frequency of the stress wave according to equation (5):

$$\tau = 1/f, \qquad (5)$$

where f is the resonance frequency of the stress wave.

Therefore the velocity of the stress wave, V, can be determined according to equation (6):

$$V = 2Lf. \qquad (6)$$

Accordingly, the calculating routine 84 calculates the velocity (V) from the measurement (L) obtained from the measurement sensor 68 or other means and transmitted to the processing unit 76, and the resonant frequency (f) located by the processing routine 80. Once the processing unit 76 has calculated the velocity (V) of the stress wave by execution of the calculating routine 84, the stress wave velocity (V) may be displayed on the display 88, and/or may be saved in memory 82 for later recall or processing.

Figure 6:
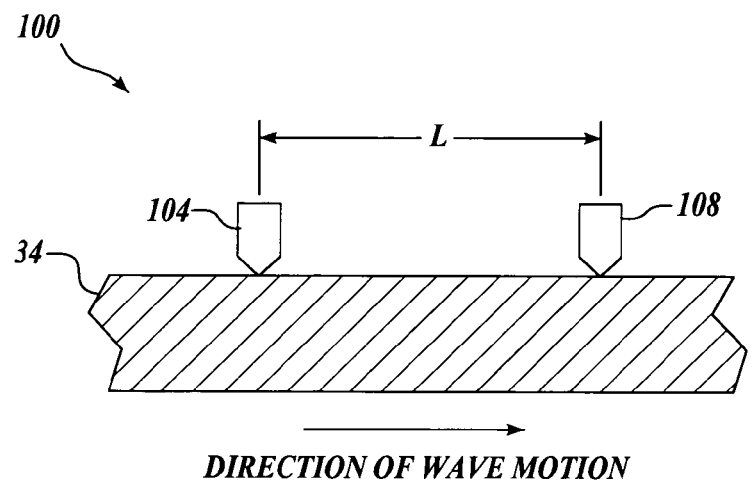
FIG. 6 is a schematic view of one embodiment of a sound wave acquisition unit.
Figure 7:
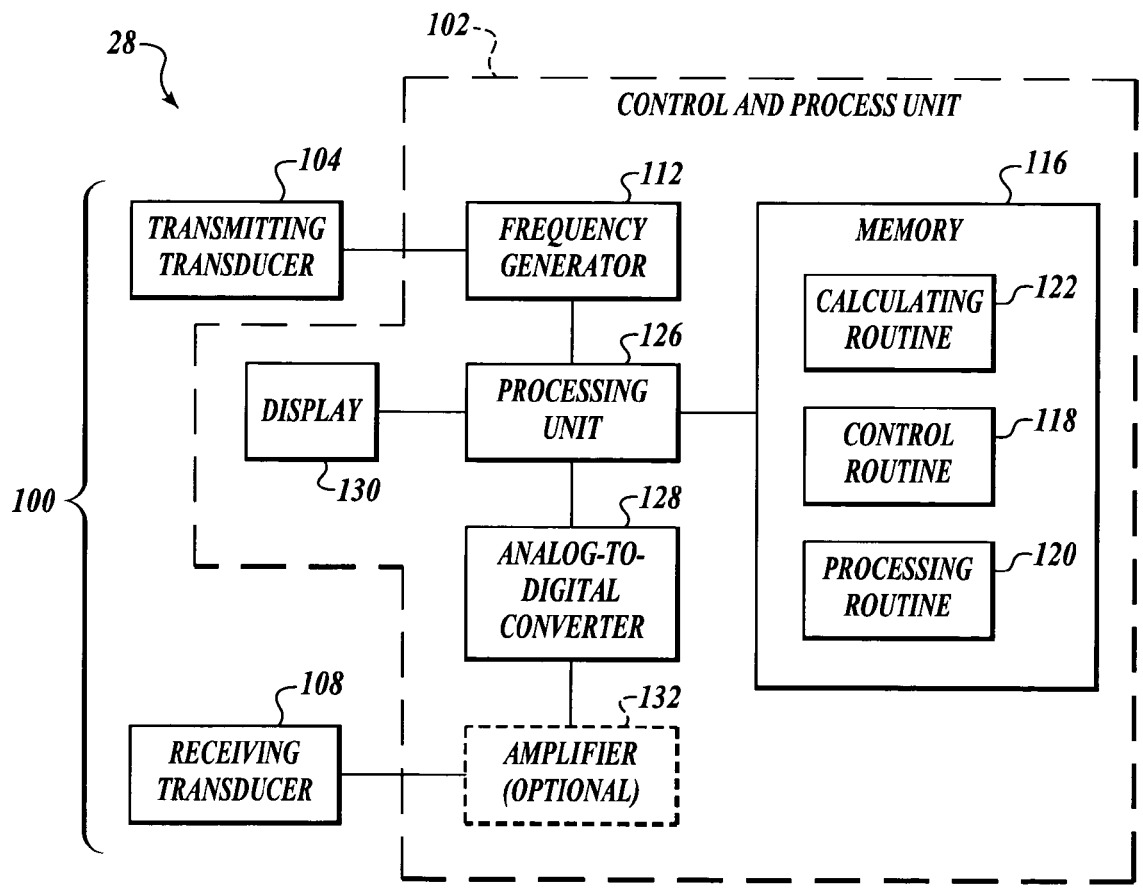
FIG. 7 is a block diagram that illustrates another embodiment of the velocity measurement sub-system.

In another embodiment of the present invention best shown in FIG. 7, the velocity testing subsystem 28 may include a sound wave acquisition unit 100 and a control and process unit 102. In the embodiment, the sound wave acquisition unit 100 includes transmitting and receiving ultrasonic transducers 104 and 108. As best shown in FIG. 6, the transmitting and receiving transducers 104 and 108 are positioned on top of the wood product 34 and spaced a fixed distance apart along its longitudinal axis (or along the direction of the grain). It will be appreciated that the incident wave transmitted by the transmitting transducer 104 progresses down the length of the wood product 34 even though the initial wave motion was transverse to the longitudinal axis of the wood product.

In one embodiment of the present invention, the transmitting and receiving transducers 104 and 108 may be built within rollers (not shown) for permitting rapid scanning of wood products as they travel longitudinally along a production line. Specifically, the transducers 104 and 108 may be encased in rollers such as may roll against the surface of the wood product as it moves in the longitudinal direction. Ultrasonic transducers encased in a wheel and suitable for use in this application with wood products are commercially available from James Instruments of Chicago, Ill. (Model C-7219) and Dapco Industries of Ridgefield, Conn. The rollers may include other features, not shown, but well known in the art, to improve transmission of the sound waves into and out of the wood product 34, such as spikes that penetrate into the wood product, or coupling fluid.

FIG. 7 is a block diagram that illustrates the control and process unit 102 constructed according to the present invention. The control and process unit 102 controls the transmitting transducer 104 and processes the signals received from the receiving transducer 108. The unit 102 generally includes a frequency generator 112, which generates the desired ultrasonic input signals, a memory 116 that stores control routine 118, a processing routine 120, and a calculating routine 122, and a processing unit 126 that executes the routines 118, 120, and 122 stored in memory 116. The frequency generator 112 is configured to generate an input frequency that is largely in the ultrasonic range but can also extend from the audio range to the ultrasonic range. The frequency generator 112 may be any suitable analog or digital frequency generator known in the art that is capable of receiving control signals from the processing unit 116 and generating the appropriate frequency waveform based in the received control signals. It will be appreciated that the frequency generator 112 may include supporting circuitry to properly process the signals received from the processing unit 126 and output a suitable signal according to the specific transducer employed.

The control and process unit 102 further includes an analog-to-digital converter 128 that receives signals from the receiving transducer 108, caused by the induced sound wave. The analog-to-digital converter 128 receives analog signals associated with the induced ultrasonic sound wave, and converts the analog signals into digital signals that may be processed by the processing unit 126. Other components known in the art may also be employed, such as a pre-amplifier (not shown), which maximizes the signal-to-noise ratio of the signal received from the receiving transducer 108. An amplifier 132 may also be optionally employed to amplify the received transducer signal.

The signals are transmitted from the analog-to-digital converter 128 to the processing unit 126, and processed by processing routine 120. The processing routine 120 may process the signals in either the time domain or the frequency domain, depending on which parameter is of interest. In the embodiment shown, the signals are processed in the time domain, and the time required for the ultrasonic sound wave to travel from the transmitting receiver 104 to the receiving 108, or time of flight (TOF), is measured. Specifically, the processing routine measures the TOF by obtaining the elapsed time between the signal peak that is indicative of the initial transmission of the ultrasonic sound wave from the transmitting transducer 104 and the signal peak that reaches a preselected threshold that is indicative of the first arrival of the ultrasonic sound wave the receiving transducer 108. The velocity may then be calculated by the calculating routine 122 by dividing the measured elapsed time or time of flight (TOF) by the distance L between the transducers 104 and 108. Once the processing unit 126 has calculated the velocity of the sound wave by execution of the calculating routine 122, the velocity may be displayed on the display 130, and/or may be saved in memory 116 for later recall or processing.

Returning to FIG. 1, the bending stiffness predicting system 20 may further include a calculating system 32 that includes known processing circuitry that is capable of calculating bending stiffness from the two measured values, density ($\rho$) and velocity (V), received from the sub-systems 24 and 28, respectively, according to Equation 1 above. The calculation of wood product bending stiffness may also be carried out manually by reading the parameter values from displays 52 and 88 or 130.

Figure 8:
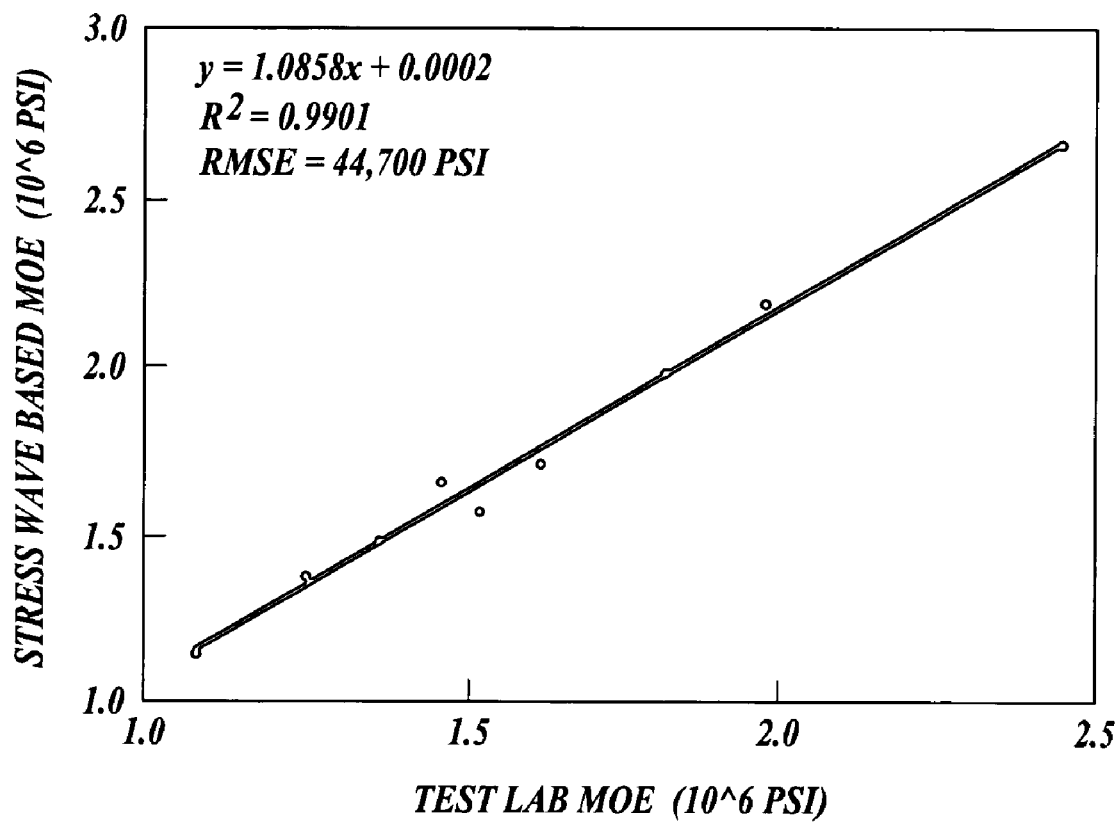
FIG. 8 is a graph depicting the calculated bending stiffness values of nine wood product samples taken from one bending stiffness predicting system of the present invention versus the bending stiffness values of the wood product samples determined by deflection stiffness testing techniques.

The results of calculating the bending stiffness in wood products according to principles of the present invention have been experimentally shown to effectively predict the bending stiffness of such wood products when subsequently tested using accepted standard methods, such as bending deflection techniques. FIG. 8 is a graph depicting the results of bending stiffness testing on nine wood product samples taken from one embodiment of the system 20 and from lab testing employing accepted bending-deflection techniques.

While each of the sub-systems 24, 28, and 32 employ a processing unit, it will be appreciated that the system 20 may employ only one system that controls each sub-system, processes all signals, and calculates all values.

While the preferred embodiments of the invention have been illustrated and described, it will be appreciated that various changes can be made therein without departing from the spirit and scope of the invention, as claimed. For example, the sequence of measuring the density and sound wave velocity is inconsequential. Therefore, the sound wave measurement may be performed prior to or after the density measurement.

The embodiments of the invention in which an exclusive property or privilege is claimed are defined as follows:

1. A method of calculating an average value of a modulus of elasticity of a dried wood-containing board, the method comprising:
   measuring the density of the board by detecting radiation absorption in the object;
   measuring the velocity of sound wave propagating through the board; and
   calculating the average value of the modulus of elasticity of the board using the density and sound wave velocity measurements.

2. The method of claim 1, wherein the sound wave is an ultrasound wave induced into the board.

3. The method of claim 1, wherein the sound wave is a stress wave induced into the board.

4. The method of claim, 1, wherein measuring the density of the board includes
emitting radiation into the board from a radiation source; and
detecting the amount of emitted radiation that travels through the board.

5. The method of claim 4, wherein measuring the density further includes
generating signals indicative of the detected radiation;
processing the generated signals; and
calculating the density of the board based on the generated signals.

6. The method of claim 1, wherein measuring the velocity of the sound wave through the board includes
determining the time of flight of an induced sound wave between a known distance; and
calculating the velocity of the induced sound wave by dividing the determined time of flight value by the known distance value.

7. The method of claim 6, wherein determining the time of flight of the sound wave includes
producing an ultrasonic sound wave in the board by a transmitting transducer, the ultrasound wave traversing through the board along the board longitudinal axis;
generating signals with a receiving transducer positioned a known distance from the transmitting transducer, the generated signals being generated by the receiving transducer based on the produced ultrasonic sound wave; and
processing the signals generated by the receiving transducer in the time domain, the processed signals resulting in a time value indicative of the time of flight of the ultrasonic sound wave between the transmitting and receiving transducers.

8. The method of claim 1, wherein measuring the velocity of the sound wave through the board includes
producing a moving stress wave within the board by impacting the board along its longitudinal axis, causing the board to freely vibrate at a harmonic resonance frequency;
sensing the stress wave as the stress wave propagates through the board with a transducer, and generating signals associated with the stress wave;
processing the signals generated by the transducer, the resonant frequency of the board obtained by processing the transducer signals; and
determining the, stress wave velocity of the board.

9. The method of claim 8, wherein processing the signals generated by the transducer includes
converting the signals received from the transducer into a frequency spectrum; and
locating the resonant frequency by analyzing the frequency spectrum.

10. The method of claim 8, wherein determining the stress wave velocity of the board includes
obtaining the longitudinal dimension value of the board;
obtaining the resonant frequency value of the induced stress wave; and
calculating the stress wave velocity through the board based on the longitudinal dimension value and the resonant frequency value.

11. A method for calculating the average bending stiffness in a dried wood product, comprising:

emitting radiation in the direction of the wood product transverse to the longitudinal axis thereof;
detecting radiation that passes through the wood product;
determining the density of the wood product based on the detected radiation;
inducing a sound wave into the wood product;
sensing the induced sound wave;
determining the velocity of the induced sound wave based on the sensed induced sound wave; and
calculating the average bending stiffness of the wood product based on the determined density and determined velocity.

12. The method of claim 11, wherein the sound wave is induced by an impactor.

13. The method of claim 11, wherein the sound wave is induced by an ultrasonic transducer.

14. A system for non-destructively calculating average bending stiffness in a dried wood product, comprising:
a density measurement sub-system including a radiation source positioned transverse to the longitudinal axis of the wood product and a radiation detector positioned on the side of the wood product opposite the radiation source, the radiation detector generating signals indicative of detected radiation, wherein the generated signals are processed to calculate the density of the wood product; and
a velocity measurement sub-system including a sound wave device that induces a sound wave in the wood product and a receiving sensor that measures the sound wave in the wood product and generates signals indicative thereof, wherein the receiving sensor generated signals are processed to calculate the velocity of the induced sound wave;
wherein the average bending stiffness in the wood product is calculated based on the calculated sound wave velocity from the velocity measurement sub-system and the density measurement from the density measurement sub-system.

15. The system of claim 14, wherein the velocity measurement and the density measurement sub-systems each includes a processing unit, the density measurement processing unit communicating with the radiation source and the radiation detector and executing a stored routine that calculates the density of the wood product based on the absorption signals generated by the radiation detector; and the velocity measurement processing unit receiving signals from the receiving sensor and executing a stored routine that calculates the velocity of the induced sound wave based on the signals received from the receiving sensor.

16. The system of claim 15, wherein the velocity measurement processing unit converts the signals received from the receiving sensor into a frequency spectrum and locates the resonant frequency of the induced sound wave.

17. The system of claim 15, wherein the velocity measurement processing unit measures the time of flight of the induced sound wave between the sound wave device and the receiving sensor.

18. The system of claim 15, further comprising a calculating unit that receives the velocity value calculated by the velocity measurement sub-system and the density value calculated by the density measurement sub-system, and calculates a resultant value that is indicative of the average bending stiffness of the wood product.

19. The system of claim 14, wherein the sound wave device of the velocity sub-system includes an impactor that strikes the end of the wood product, causing the sound wave to propagate through the wood product.

20. The system of claim 14, wherein the sound wave device of the velocity sub-system includes an ultrasonic transducer in contact with the wood product.

* * * * *